United States Patent [19]

Guimont et al.

[11] Patent Number: 4,560,779

[45] Date of Patent: Dec. 24, 1985

[54] PREPARATION AND POLYMERIZATION OF OXETHER-1

[75] Inventors: John M. Guimont; Gerald E. Manser, both of Cupertino; Donald L. Ross, Los Altos, all of Calif.

[73] Assignee: The United States of America as represented by the Secretary of the Air Force, Washington, D.C.

[21] Appl. No.: 400,179

[22] Filed: Jul. 20, 1982

[51] Int. Cl.$^4$ ............................................. C07D 305/06
[52] U.S. Cl. ..................................... 549/510; 528/417
[58] Field of Search .......................................... 549/510

[56] References Cited

U.S. PATENT DOCUMENTS

| | | | |
|---|---|---|---|
| 2,722,520 | 11/1955 | Hulse | 260/2 |
| 3,335,155 | 8/1967 | Linden et al. | 549/551 |
| 3,449,369 | 6/1969 | Berezin | 260/333 |
| 3,576,802 | 4/1971 | Luders et al. | 260/240 |
| 3,594,348 | 7/1971 | Maar et al. | 260/47 |
| 3,636,060 | 1/1972 | Frankel et al. | 549/551 |
| 3,652,600 | 3/1972 | Grakauskas | 549/551 |
| 3,907,907 | 9/1975 | Frankel et al. | 549/551 |
| 4,092,336 | 5/1978 | Frankel et al. | 549/551 |
| 4,168,273 | 9/1979 | Witucki et al. | 549/551 |

OTHER PUBLICATIONS

L. Zeldin et al, Jour. Am. Chem. Soc., vol. 79 (1957) pp. 4708–4716.

Primary Examiner—Norma S. Milestone
Attorney, Agent, or Firm—Donald J. Singer; William J. O'Brien

[57] ABSTRACT

The present invention provides a method for synthesizing a novel oxether-1 monomer by a two step reaction scheme which involves effecting a reaction between 3-methyl-3-hydroxymethyl oxetane and 1,1,1-trinitroethane to form an intermediate reaction product which in turn is reacted with methyl iodide to produce the oxether-1 monomer. The monomer is easily polymerized using conventional polymerization techniques to produce a poly(oxether-1) polyol useful as a binder component in smokeless propellants and explosives.

1 Claim, 5 Drawing Figures

NMR SPECTRUM OF POLY(OXETHER-1), CDCl$_3$ $$\begin{array}{c} \phantom{+O-}\overset{4}{C}H_2-O-\overset{5}{C}H_2-C(NO_2)_2-\overset{2}{C}H_3 \\ \overset{3}{+O-CH_2}-\underset{\underset{\underset{1}{CH_3}}{|}}{\overset{|}{C}}-CH_2+_n \end{array}$$

$M_w = 6,800$
$M_n = 3,900$
$Q = 1.7$
HYDROXYL EQUIVALENT WEIGHT = 2,100

GPC OF POLY(OXETHER-1)

PREPARATION AND POLYMERIZATION OF OXETHER-1

STATEMENT OF GOVERNMENT INTEREST

The invention described herein may be manufactured and used by or for the Government for governmental purposes without the payment of any royalty thereon.

BACKGROUND OF THE INVENTION

This invention relates in general to a novel, polymerizeable, oxetane monomer; its method of preparation; and its polymerization. In a more particular aspect, this invention concerns itself with the novel synthesis of 3-methyl-3-(2,2-dinitropropoxymethyl)oxetane and the nitropolymer resulting from its polymerization.

The present interest and increased utilization of smokeless propellants have spawned a considerable research effort in an attempt to extend the technological basis required to develop the chemistry and techniques necessary to produce newer and more efficient materials for use in the fabrication and formulation of such propellants.

One of the principle objectives of this research effort involves the synthesis and evaluation of energetic polymers having the ultimate potential of yielding practical solid propellants which have aging, operational temperature limits, and performance characteristics that are superior to presently available, tactical, minimum smoke propellants of the nitrite ester/HMX-RDX type. Obviously, the development of propellants which are smokeless, or relatively free from smoke, during their operational phase constitutes an important tactical advantage since their use substantially minimizes the detection of devices using such propellants.

In attempting to attain the research objective referred to above, it was found unexpectedly that a novel, energetic, cyclic ether prepolymer, prepared in accordance with the method of this invention, could be polymerized to produce an energetic nitropolymer useful as the polymeric or binder constituent of a smokeless propellant.

SUMMARY OF THE INVENTION

The present invention concerns itself with a novel method for synthesizing a polymerizeable, nitroalkyl-substituted oxetane and to the resultant 3-methyl-3-(2,2-dinitropropoxymethyl)oxetane (preferably and hereinafter referred to as oxether-1) monomer produced thereby. The oxether-1 monomer of this invention is prepared by a two step reaction sequence as illustrated by the following equation:

$$C(NO_2)_3CH_3 + O\underset{CH_3}{\overset{CH_2OH}{\diamond}} \xrightarrow[(1)]{KOH}$$

$$O\underset{CH_3}{\overset{CH_2OCH_2C(NO_2)_2K}{\diamond}} \xrightarrow[(2)]{CH_3I}$$

$$O\underset{CH_3}{\overset{CH_2OCH_2C(NO_2)_2CH_3}{\diamond}}\quad (I)$$

The invention also concerns itself with the synthesis of poly(oxether-1), a novel dinitropolymer found to be especially useful as the polymeric or binder constituent of energetic propellants.

It possesses a molecular weight ranging from about 1000 to 11000 and is represented by the following structural formula:

$$\mathrm{+O-CH_2-\underset{\underset{CH_3}{|}}{\overset{\overset{CH_2-O-CH_2-C(NO_2)_2-CH_3}{|}}{C}}-CH_2\rightarrow_n} \quad (II)$$

wherein n is an integer of from about 6 to 65.

The poly(oxether-1) possesses chemical stability at −65° F. to +165° F. with glass transition temperatures of less than −65° F. with a suitable plasticizer. It is further characterized by having reproducible functionalities of two or greater, reproducible and controllable molecular weights, and it is liquid or low melting with a high solubility in plasticizers.

Accordingly, the primary object of this invention is to develop a novel poly(oxether-1) polymer useful as the energetic polymeric constituent of smokeless propellant compositions.

Another object of this invention is to provide a novel 3-methyl-3-(2,2-dinitropropoxymethyl)oxetane(oxether-1) which is readily polymerizeable.

Still another object of this invention is to provide a method or reaction scheme for effecting the synthesis of 3-methyl-3-(2,2-dinitropropoxymethyl)oxetane(oxether-1).

The above and still other objects and advantages of the present invention will become more readily apparent upon consideration of the following detailed disclosure thereof when considered in light of the accompanying drawings.

DESCRIPTION OF THE PREFERRED EMBODIMENTS

Figure 1:
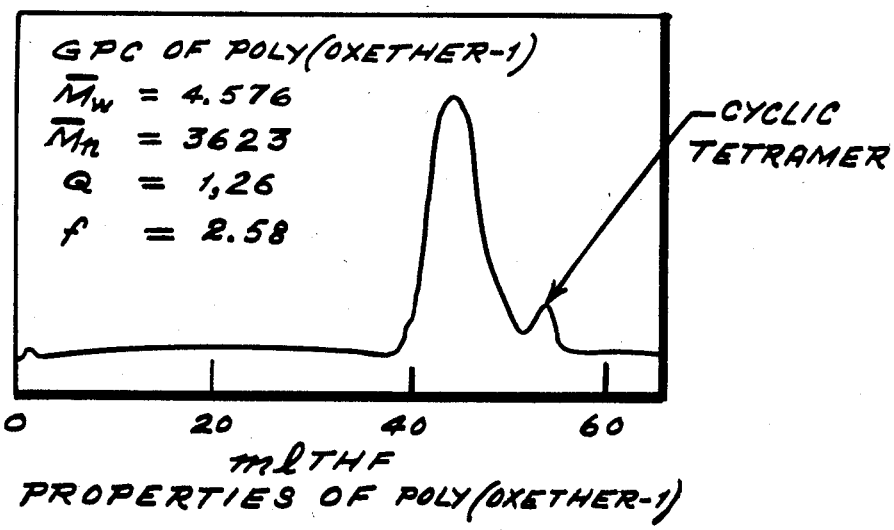
FIG. 1 is a graphical illustration showing the properties of a poly(oxether-1) with a molecular weight of 4576.

In accordance with this invention, it has been found that the above defined objects can be accomplished by synthesizing a novel 3-methyl-3-(2,2-dinitropropoxymethyl)oxetane monomer, hereinafter referred to as oxether-1. The synthesis of the novel oxetane monomer of this invention was accomplished by a novel, two-step reaction sequence in which a potassium hydroxide solution of 3-methyl-3-hydroxymethyl oxetane was first reacted with 1,1,1-trinitroethane. The product of this first reaction was then heated with methyl iodide to produce the oxether-1 monomer. Examples 1 and 2 which follow, further illustrate, in specific detail, the particular method of this invention that is utilized to synthesize oxether-1.

EXAMPLE 1

A solution of 77 g of potassium hydroxide in 500 g of 3-methyl-3-hydroxymethyl oxetane was mixed with 2500 ml of diethylether. To this mixture was added a solution of 113 g of 1,1,1-trinitroethane in 400 ml of ether over a period of one hour at 25° C. The reaction mixture was refluxed for 4 hours, cooled to 25° C., and filtered. The filtered solid was washed with ether, and then added to 2000 ml of acetone. To the acetone mixture was added 389 g of methyl iodide, and the acetone mixture was refluxed for 2 days. After cooling, the reaction mixture was filtered and the acetone was removed in a vacuum. The residue was dissolved in ether and washed three times with 5% aqueous sodium bicarbonate and twice with one molar aqueous sodium thiosulfate. The ether solution was dried with magnesium sulfate and removed in vacuum. The crude product was chromatographed on neutral alumina with chloroform to yield 61 g (38% yield based on trinitroethane) of 3-methyl-3-(2,2-dini-tropropoxymethyl)oxetane(Oxether-1). IR 2850, 2950 (S, CH), 1670 (S,$NO_2$) 1110 (m, COC); H nmr ($CDCL_3$), 1.29 (S,$CH_3$), 2.2 (S,$CH_3CNO_2$), 3.63 (S, $CH_2O$), 4.36 (m, $CH_2CNO_2$ and $CH_2$ ring).

Analysis Calcd. for $C_8ZH_{14}N_2O_6$: C, 41.02; H, 5.98; N. 1196. Found C, 39,93; H, 5.86; N, 11.49.

EXAMPLE 2

95 g (1.44 moles) of 85% potassium hydroxide was dissolved in 380 g (3.72 moles) of 3-methyl-3-hydroxymethyloxetane. Then 2 liters of diethylether was added to a 250-g aliquot of this solution, and 116.8 g 10.7 mole) trinitroethane in 500 ml of diethyl ether was added over 2 hours with stirring. The resulting red-orange suspension was refluxed for 2 hours. The solid was filtered off and washed with two one-liter portions of ether and acetone. It was suspended in 2 liters of acetone and 400 g of methyl iodide was added in one portion. The suspension was refluxed with stirring for 4 days. The acetone was removed, and the residue was mixed with dichloromethane. Solid potassium iodide was filtered off, and the resulting solution was washed with potassium iodide and sodium thiosulfate solutions to remove free iodine. The solution was then washed with aqueous sodium bicarbonate, and bine, and dried over magnesium sulfate. After concentration, the yield was 81.3 g (50% on trinitroethane) of crude oxether-1. Purification on silica was incomplete. Further chromatography on neutral alumina with chloroform as the mobile phase gave 22 g of oxether-1 (14% based on trinitroethane).

In carrying out the method of this invention, as exemplified in Examples 1 and 2, one mole of KOH is added to 10 moles of the oxetane. This gives one mole of a potassium salt of the oxetane, leaving nine moles of the oxetane which functions as a solvent for the preparation of the potassium salt. One or two moles (perferably one mole) of 1,1,1-trinitroethane is then added which gives one mole of a potassium adduct. Then, one to two moles of methyl iodide are added to the adduct. The iodide replaces the potassium giving the oxether-1 monomer of this invention. The diethylether solvent, used in the reaction scheme, seems to enhance the yield.

The synthesis route disclosed above for preparing oxether-1 provides a monomer that can be polymerized in high yield with molecular weights ranging from about 1100 to 11,000 by conventional polymerization techniques such as those disclosed by Dreyfus et al in Sci-Chem, A7(7), 1361 (1973) and Dreyfus et al in J. Polym. Sci., Part A-1 4, 2179 (1966).

Figure 5:
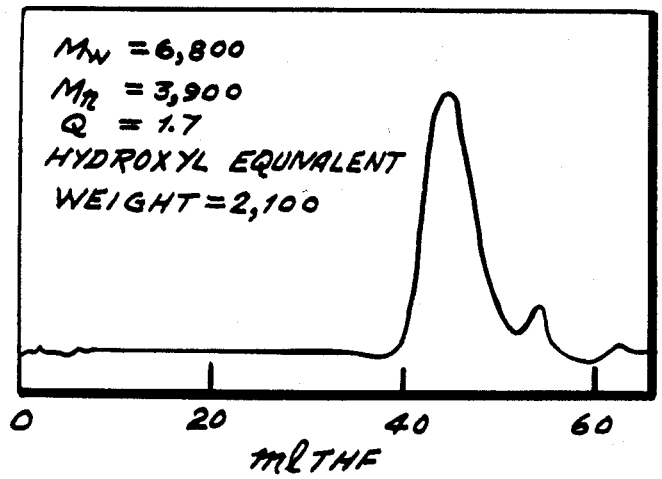
FIG. 5 is a graphical illustration showing the GPC and other properties of a poly(oxether-1) with a molecular weight of 6800.

The results of studies of the polymerization of oxether-1 show that (1) it is a reactive monomer that is readily polymerized with a boron trifluoride diethyl etherate complex with no added co-catalyst; (2) the molecular weight of polymers from oxether-1 seems to reach a limiting molecular weight of about 11,000; (3) it is possible to control the molecular weight and the molecular weight distribution of poly(oxether-1) by varying the catalyst and co-catalyst concentrations and the reaction time; and (4) both water (effectively a diol) and 1,1,1-tris-(hydroxymethyl)ethane are effective co-catalysts. In a small scale polymerization of oxether-1, a nitro-alkyl substituted polyol of molecular weight 6800 (hydroxyl equivalent weight 2100) was recovered in 98% conversion; a gumstock was prepared by curing with tolylene diisocyanate. The GPC of this particular polymer is illustrated in FIG. 5.

Results of the boron trifluoride diethyl etherate catalyzed polymerization of oxether-1 with water, 1,4-butanediol (BDO) and TME as co-catalysts are summarized in Tables I and II. All reactions were run at 20 wt% oxether-1 in dichloromethane solvent. Conversions in runs 2–16 were greater than 90% and recoveries were greater than 85%. The products from each run were evaluated by gel permeation chromatography (gpc).

In one polymerization experiment, run 2 of Table I, a 20 wt% solution of oxether-1 was treated with boron trifluoride etherate (100:3.3 monomer:catalyst) at 22° C. for 3 hours. GPC analysis of the crude product showed that the major component was a polymer with a fairly narrow molecular weight range centered at about 5000. The properties of this polymer are shown in FIG. 1. Small amounts of tetramer and dimer were present along with an unknown impurity in the monomer. The results of this run were very encouraging since oxether-1 appears to polymerize readily with the boron trifluoridediethylether complex.

Figure 4:
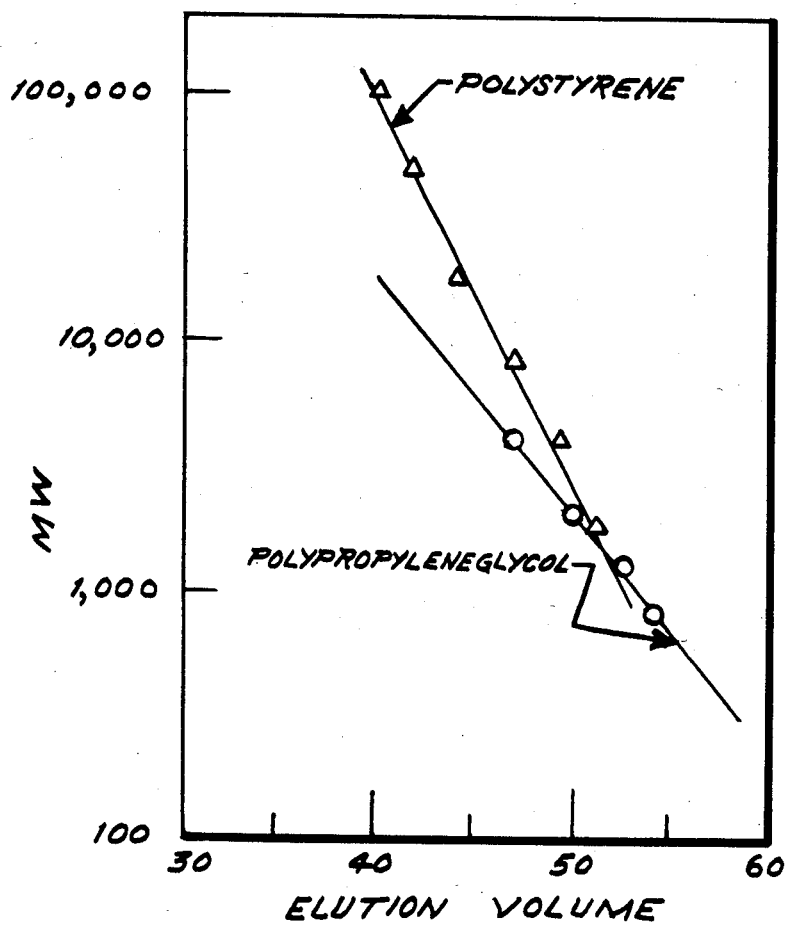
FIG. 4 is a graphical illustration showing the calibration curves for GPC.

The chromatograms indicated that some material was being exlucded at the upper molecular weight limit of the column set. Two additional columns were added, to give a set comprising seven Waters Associates M-Styragel columns: Two 100-Å, two 500-Å, one $10^3$-Å, one $10^4$-Å, and one $10^5$-Å columns. They were calibrated with sets of polypropylene glycol (PPG) and polystyrene (PS) standards which are illustrated in FIG. 4. The plots of log MW versus elution volume for the two sets of standards give different calibration curves.

The differences between the calibration curves for polystyrene and polypropylene glycol, as shown in FIG. 4, point out an easily neglected characteristic of GPC. Gel permeation chromatography separates materials on the basis of the effective size of the molecules in solution, not the molecular weight of the material. Molecular structure and solvent are important variables in GPC. For a given polymer, the relationship between molecular size and molecular weight is constant but the proportionality constant is different for different polymers in a given solvent or the same polymer in different solvents. Ideally, the GPC should be calibrated with the polymer of interest in the solvent of interest. Calibration with a known material is effective only if it is a good model for the unknown material to be examined. Because PPG is a better model for poly(oxether-1) than PS, we believe that the actual molecular weights of the polymers obtained are better approximated by the PPG curve. Molecular weights reported in runs 2 to 16 were calculated by using the PPG curve and then extrapolating to higher molecular weights. The extrapolation should be valid because the curve for PS is linear to $MW = 7 \times 10^5$, and the PPG curve is linear over the range of standards available. Values calculated from the GPC are number average molecular weight, $M_n$, weight average molecular weight, $M_w$, and the polydispersity, Q, which is the ratio $\overline{M}_w/\overline{M}_n$, and measures the broadness of the molecular weight distribution. The molecular weights reported for runs 2 to 16 were calculated from quantitative GPC data in different ways. The first method used data from the entire chromatogram, including the area for the residual monomer present in the sample. In the second method, the GPC was truncated at the minimum preceding the monomer peak, and the area for the monomer was thereby neglected. As expected, molecular weight values are lower by method one than by method two. The effect is greatest on the number average molecular weight, which is dependent on the number of molecules of a given size. As a result, Q is generally much smaller by method two. Although the values derived by method two are only approximate because they are calculated, it is believed they better represent the polymer. In a large sample, the residual monomer will be extracted before the polymer is evaluated. The approximation used in method two is equivalent to cleaning up the product, and determining the GPC and molecular weight.

The polymerization runs in Tables I and II are divided into three distinct groups based on the co-catalyst used in the run. In the first group of experiments (runs 2-5), no co-catalyst was added. In the second group (runs 6-12), varying amounts of water were added. In the third group of experiments (runs 13-16), 1,1,1-tris(hydroxymethyl)ethane (TME) was added as the co-catalyst.

In the first group of experiments, efforts were made to eliminate fortuitous water. The solutions and the apparatus were carefully dried and the reaction was completed under a nitrogen blanket. It has been shown that total exclusion of water, or other proton sources, in polymerizations catalyzed with boron trifluoride prevents polymerization from occurring. Since in each of these runs the conversion was 85% or more, some water was present. In this group, there are two kinds of experiments. In the first, the variable is reaction time (runs 2 and 5). It appears as though reaction time has no effect on the molecular weight of the polymer. In other experiments (runs 2-4), the variable is catalyst load. Increasing the catalyst ten-fold (run 4 versus run 2) decreased the molecular weight of the product by about 1000 units (equivalent to 4 monomer units).

In the second group of experiments, an amount of water was added to each experiment. The water ranged from 10 mol% in runs 6 and 7 to as much as 200 mol% relative to boron trifluoride in runs 10-12. The results of these experiments indicate that when low levels of water are added, the molecular weights of the polymer are nearly the same as in runs with no added water (runs 6 and 7 versus runs 2 and 4). When the water concentration is increased to be equimolar to the boron trifluoride, a significant drop in molecular weight occurs (run 9 versus run 2). The $M_w$ dropped from 11,000 to 6,300. Increasing the water to twice the catalyst decreased the molecular weight further to 4,600 (run 10). Decreasing the catalyst and co-catalyst load to 100:1:2 (runs 11) compared to 100:3.3:6.6 (run 9) increased the molecular weight to 6,200, indicating an effect of catalyst loading on molecular weight. Run 12 was allowed to proceed for 1 hour, twice as long as run 11, and the molecular weight was 6,800, slightly higher, indicating a possible effect of reaction time on molecular weight.

In the third group 1,1,1-tris(hydroxymethyl)ethane (TME) was substituted for water as the co-catalyst. The objective here was to produce an isocyanate-curable polyol with a minimum of two hydroxyl groups per molecule because use of water as the co-catalyst invariably gave a functionality 2. Because TME was not completely soluble in these runs, the exact co-catalyst concentration is unknown. To exmaine a product more closely, run 25 was scaled from 300–500 mg to 15 g of monomer. After methanol wash to remove low molecular weight material, the polyol molecular weight was 6800 with a functionality of approximately 3. A 10 g aliquot of this viscous polyol was mixed at room temperature with 0.4 g tolylene diisocyanate and 10 μl of dibutyltindilaurate (T12) catalyst in dichloromethane solution. The solvent was removed in a vacuum oven and the mix cured for 48 hours at 65° C. The resulting gumstock was rigid and somewhat brittle. Run 13 duplicated run 12 except that TME replaced water. The conversion and the polymer molecular weight decreased slightrly. In runs 14–16, the TME and boron trifluoride concentration were decreased by one-half. TME remained only partially soluble. The products from these runs were similar to one another, and higher in molecular weight than run 13 when the monomer peak was eliminated from the calculation. The conversion increased for longer reaction times (run 16 versus run 15) and the molecular weights were the same when corrected for monomer. The effect of residual monomer is very pronounced in this pair of runs. In run 15 (lower conversion, less time), $M_w = 4,100$, $M_n = 360$, and $Q = 11.5$ while in run 16 $M_w = 5,600$, $M_n = 1,100$, and $Q = 5.4$. When the monomer peak is eliminated from the calculation, the values change to $M_w = 6,100$, $M_n = 3,300$, and $Q = 1.8$ for un 15, and $M_w = 6,200$, $M_n = 3,700$, and $Q = 1.7$ for run 16. The effect is most pronounced on Q. When the monomer is eliminated, the molecular weights and molecular weight distributions are nearly identical.

Figure 2:
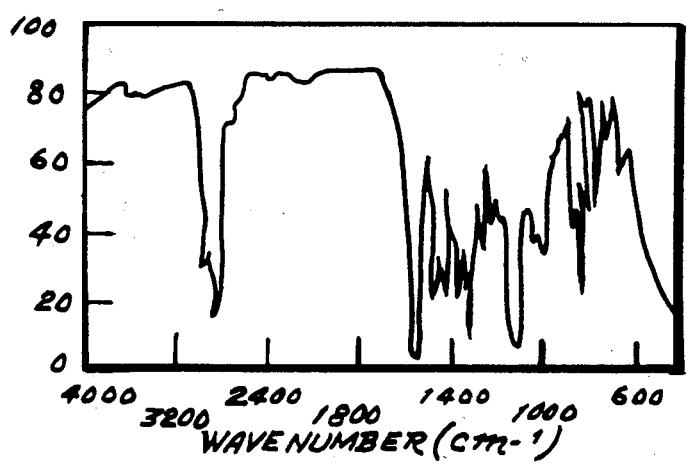
FIG. 2 is a graphical illustration showing the infrared spectrum of poly(oxether-1)
Figure 3:
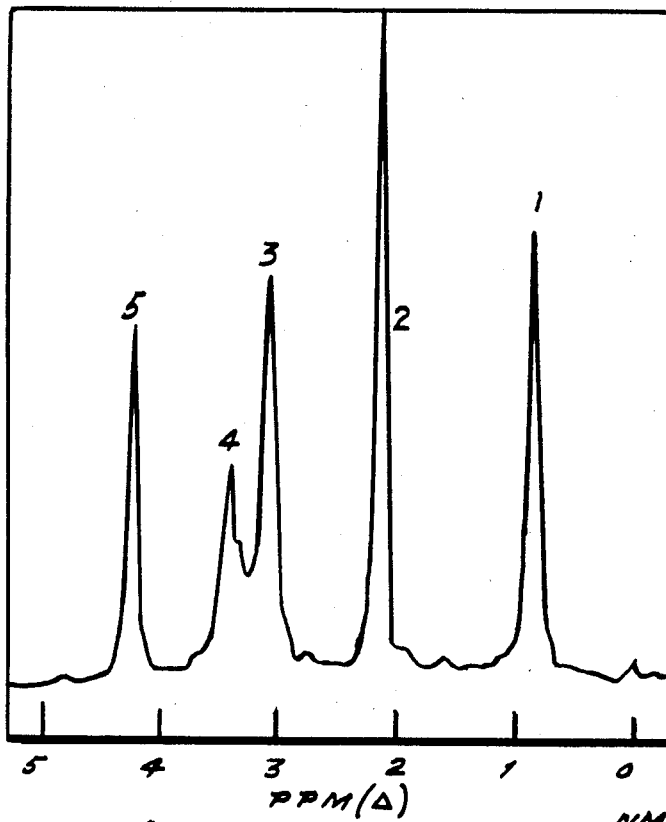
FIG. 3 is a graphical illustration showing the NMR spectrum of poly(oxether-1)

As a result of the polyermization study, the reaction was scaled from 300 mg to 2 g of monomer per run. These larger runs were completed with a freshly prepared lot of oxether-1. The stoichiometry for these runs duplicated run 16. That is, monomer:BF$_3$·Et$_2$O:TME = 100:0.5:1. The monomer concentration was 20 wt% in dichloromethane, and the reaction was run at ambient temperature. A series of runs (18-22) was completed under these conditions. The first of these runs (18,19) showed very little conversion. Increasing the reaction time had no effect on the conversion. An evaluation of the reaction conditions and reagents revealed that the monomer was not pure. The impurity (a hydroxyl-containing material) apparently was inhibiting the polymerization or deactivating the catalyst so that no reaction occurred. After several attempts to purify the monomer, it was successfully purified on neutral alumina with reagent grade chloroform as the eluant. Following this chromatography, the oxether-1, as illustrated in FIGS. 2, 3 and 5 showed no hydroxyl in the ir, the nmr was very clean and sharp, and GPC showed only a single, very symmetrical peak. Run 23 (300 mg, conditions like run 16) showed a 98% conversion to polyol by GPC. Run 24 (5 g) and run 25 (15 g) duplicated run 23 in all respects. The products from runs 24 and 25 were combined and characterized by GPC and acetylation as shown in FIG. 5 which also defines the $M_w$, $M_n$ and Q properties of the resulting polyol. A 10 g aliquot of this polyol was mixed at room temperature with 0.4 g toluene diisocyanate and 10 μl dibutyltindilaurate in dichloromethane solution. The solvent was removed in a vacuum oven, and the mix was cured 48 hours at 65° C. The resulting gumstock was rather tacky and soft and contained a few bubbles. After the material was left standing, some residual solvent evaporated, more bubbles developed, and the material became more rigid and somewhat brittle.

The polymerization techniques referred to in Tables I and II are further illustrated by Example 3 as follows:

EXAMPLE 3

In a typical polymerization of oxether-1, an aliquot of 20 wt% oxether-1 was weighed into a small (10 ml) resin kettle that had been oven dried at 120° C. for 3 hours and purged with dry nitrogen. The kettle was fitted with a drying tube and septum for introducing the reagents. The required amount of co-catalyst was added by syringe or as a solid. Borotrifluoride-diethylether complex was added by microliter syringe, and the solution was magnetically stirred for the required time. The reaction was then quenched with aqueous ammonium hydroxide and allowed to stir for 30 minutes. Excess dichloromethane was added, and the two-phase mixture was transferred to a separatory funnel. The solution was washed twice with 5% bicarbonate solution and saturated brine. The combined aqueous phases were saturated with sodium chloride, and back-extracted with dichloromethane. All organic solutions were combined, dried over magnesium sulfate, and solvent was removed. Typical recoveries based on starting monomer were 95% or greater. Analysis was by GPC.

TABLE I

POLYMERIZATION OF OXETHER-1

| | | | GPC Results | | | | | |
|---|---|---|---|---|---|---|---|---|
| | | Mole Ratio Monomer | Including | | | Excluding Low MW Material | | |
| Run | Co-Catalyst | Catalyst: Co-Catalyst | $M_w$ (000) | $M_n$ (000) | Q | $M_w$ (000) | $M_n$ (000) | Q |
| 2 | None | 100:3.3:0 | 10.8 | 2.8 | 3.9 | 11.0 | 5.2 | 2.1 |
| 6 | $H_2O$ | 100:3.3:0.33 | 10.1 | 1.8 | 5.8 | 10.7 | 5.7 | 1.9 |
| 9 | $H_2O$ | 100:3.3:3.3 | 6.0 | 1.4 | 4.2 | 6.3 | 3.9 | 1.6 |
| 10 | $H_2O$ | 100:3.3:6.6 | 4.1 | 0.7 | 5.5 | 4.6 | 2.7 | 1.7 |
| 11 | $H_2O$ | 100:1:2 | 3.4 | 0.26 | 13.2 | 6.2 | 3.9 | 1.6 |
| 27 | $H_2O$ | 100:1:2 | 4.6 | 0.5 | 8.8 | 5.6 | 4.0 | 1.4 |
| 28 | $H_2O$ | 100:8:16 | 4.9 | 1.2 | 4.3 | 6.3 | 4.2 | 1.5 |
| 29 | $H_2O$ | 100:4:8 | 2.5 | 0.7 | 4.3 | 3.8 | 2.4 | 1.6 |
| 31 | $H_2O$ | 100:2:4 | 4.0 | 0.7 | 5.5 | 5.1 | 3.6 | 1.4 |
| 15 | TME[a] | 100:0.5:1 | 4.1 | 0.4 | 11.5 | 6.1 | 3.3 | 1.8 |
| 16 | TME | 100:0.5:1 | 5.6 | 1.1 | 5.4 | 6.2 | 3.7 | 1.7 |
| 25 | TME | 100:0.5:1 | Not Analyzed | | | 6.8 | 3.9 | 1.7 |
| 35 | BDO[b] | 14:2:1 | Not Analyzed | | | 3.9 | 3.1 | 1.2 |
| 36 | BDO + TMP[c] | 14.3:2.5:0.5 + 0.5 | 2.5 | 1.5 | 1.6 | 3.3 | 2.7 | 1.2 |

[a]1,1,1-Tris(hydroxymethyl)ethane
[b]1,4-Butanediol
[c]1,1,1-Tris(hydroxymethyl)propane

TABLE II

POLYMERIZATION OF OXETHER-1

| | | | | | GPC Results | | | | | |
|---|---|---|---|---|---|---|---|---|---|---|
| | Added Co- | Monomer: Catalyst: | Time | Elution Volume | Including Residual Monomer | | | Excluding Residual Monomer | | |
| Run | Catalyst | Co-catalyst | (hr) | (ml) | $M_w$ | $M_n$ | Q | $M_w$ | $M_n$ | Q |
| 3 | None | 100:10:0 | 3.0 | 41.2 | 10.4 | 1.4 | 7.3 | 11.1 | 4.8 | 2.3 |
| 4 | None | 100:33:0 | 3.0 | 41.6 | 9.2 | 1.3 | 7.1 | 9.9 | 5.6 | 1.8 |
| 5 | None | 100:3.3:0 | 0.5 | 41.6 | 11.3 | 4.3 | 2.6 | 11.3 | 6.7 | 1.7 |
| 7 | $H_2O$ | 100:33:3.3 | 0.5 | 41.2 | 9.5 | 0.76 | 12.6 | 11.1 | 5.6 | 2.0 |
| 8 | $H_2O$ | 100:100:100 | 0.5 | 45.6 | 3.4 | 0.54 | 6.2 | 4.2 | 1.7 | 2.5 |
| 12 | $H_2O$ | 100:1:2 | 1.0 | 44.0 | 6.3 | 1.0 | 6.2 | 6.8 | 4.6 | 1.5 |
| 13 | TME | 100:1:2 | 1.0 | 46.4 | 3.8 | 0.67 | 5.6 | 4.4 | 2.7 | 1.6 |
| 14 | TME | 100:0.5:1 | 3.0 | 44.8 | 4.6 | 0.63 | 7.4 | 5.9 | 3.3 | 1.8 |

As was stated heretofore, the products of this invention have been found to be useful as the binder component for explosives and energetic, solid, polyurethane-cured propellants instead of the conventional polypropylene glycol binders employed heretofore. Such propellants generally comprise a mixture of an inorganic oxidizer dispersed in the matrix of the polyol component which acts as a binder. Other conventional additives such as plasticizers, stabilizers, burning rate modifiers, anti-oxidants, etc., may be employed, if desired or necessary. Curing or cross-linking agents may also be added to effect curing, when a polyol pre-polymer is utilized as the binder component. The following example illustrates the manner in which the polymer of this invention is utilized in a propellant.

EXAMPLE 4

| COMPONENT | AMOUNT (% BY WT) |
|---|---|
| Oxether-1 (Prepolymer) | 6 to 10 |
| N-100 (Cross-linking and Curing Agent)[a] | 1 to 2 |

-continued

| COMPONENT | AMOUNT (% BY WT) |
|---|---|
| HMX (Oxidizer)[b] | 60 to 80 |
| BTTN (Plasticizer)[c] | 3 to 10 |
| NG (Plasticizer)[d] | 3 to 10 |
| Lead Citrate (Additive) | 1 |
| Zirconium Carbide (Combustion Stabilizer) | 1 |
| Carbon (Combustion Stabilizer) | 0.05 to 0.1 |

[a] a trifunctional isocyanate manufactured by the Mobay Chemical Corporation, Pittsburgh, Penn.
[b] Cyclotetramethylene tehanitramine
[c] Butanetriol trinitrate
[d] Nitroglycerin In preparing the formulation of Example 4, the oxether-prepolymer and plasticizer are placed in a Perkins blender. The HMX is slowly added followed by the remaining ingredients until well mixed. The N-100 is then added with mixing at from room temperature to about 50° C. until well mixed. The mixture is then vacuum cast in a suitable mold to a predetermined shape followed by curing at a temperature of from about 60° to 100° C. until fully cured, usually a period of time taking from about 24 to 48 hours.

In considering the foregoing detailed description, it is evident that the present invention provides a novel nitro-substituted oxetane, specifically oxether-1, that is readily polymerized under a variety of conditions. The resulting polymeric ether containing polyol can be cured into a urethane gumstock, using tolyol diisocyanate for example, and used as a binder component for explosives and propellants. The oxether-1 monomer of this invention was polymerized in high yield to give polymers with molecular weights in the range of 1100 to 11,000.

While the present invention has been described by reference to specific embodiments thereof, it should be understood that various modifications and alterations may be made without departing from the spirit and scope of the invention and that all such modification as are encompassed within the appended claims are intended to be included herein.

What is claimed is:

1. As a new compound, the monomer 3-methyl-3-(2,2-dinitropropoxymethyl)oxetane.

* * * * *